US 9,262,589 B2

(12) United States Patent
Potkonjak et al.

(10) Patent No.: US 9,262,589 B2
(45) Date of Patent: Feb. 16, 2016

(54) SEMANTIC MEDICAL DEVICES

(75) Inventors: Miodrag Potkonjak, Los Angeles, CA (US); Ani Nahapetian, Glendale, CA (US)

(73) Assignee: Empire Technology Development LLC, Wilmington, DE (US)

( * ) Notice: Subject to any disclaimer, the term of this patent is extended or adjusted under 35 U.S.C. 154(b) by 196 days.

(21) Appl. No.: 13/519,309

(22) PCT Filed: Apr. 13, 2010

(86) PCT No.: PCT/US2010/030952
§ 371 (c)(1),
(2), (4) Date: Oct. 15, 2012

(87) PCT Pub. No.: WO2011/129817
PCT Pub. Date: Oct. 20, 2011

(65) Prior Publication Data
US 2013/0041861 A1 Feb. 14, 2013

(51) Int. Cl.
*G06F 19/00* (2011.01)

(52) U.S. Cl.
CPC ............ *G06F 19/3418* (2013.01); *G06F 19/30* (2013.01); *G06F 19/345* (2013.01); *G06F 19/3406* (2013.01); *G06F 19/3431* (2013.01)

(58) Field of Classification Search
CPC ... G06F 19/345; G06F 19/30; G06F 19/3406; G06F 19/3418; G06F 19/3431
USPC ......................................................... 706/924
See application file for complete search history.

(56) References Cited

U.S. PATENT DOCUMENTS

| | | | |
|---|---|---|---|
| 4,202,340 A | 5/1980 | Langer et al. | |
| 5,146,228 A | 9/1992 | Irani et al. | |
| 5,506,916 A | 4/1996 | Nishihara et al. | |
| 5,868,669 A * | 2/1999 | Iliff | 600/300 |
| 7,643,142 B2 | 1/2010 | van den Engh | |
| 7,653,248 B1 | 1/2010 | Witzgall et al. | |
| 8,427,346 B2 | 4/2013 | Potkonjak | |
| 8,473,438 B2 | 6/2013 | Potkonjak | |
| 2002/0103938 A1 | 8/2002 | Brooks et al. | |
| 2003/0012400 A1 | 1/2003 | McAuliffe et al. | |
| 2003/0158468 A1 * | 8/2003 | Iliff | 600/300 |
| 2003/0212319 A1 * | 11/2003 | Magill | 600/382 |
| 2004/0068332 A1 | 4/2004 | Ben-Gal et al. | |
| 2005/0049497 A1 * | 3/2005 | Krishnan et al. | 600/437 |
| 2005/0078017 A1 | 4/2005 | Gergely et al. | |
| 2005/0131660 A1 | 6/2005 | Yadegar et al. | |

(Continued)

FOREIGN PATENT DOCUMENTS

WO  WO 2006109072 A2 * 10/2006
WO  WO-2011/129817     10/2011

OTHER PUBLICATIONS

"Electronic Implants that Dispense Medicines Via Wireless Medical Network are on the Horizon," Feb. 6, 2009. http://www.azonano.com/news.aspx?newsID=9780.

(Continued)

*Primary Examiner* — Jeffrey A Gaffin
*Assistant Examiner* — Thomas Fink
(74) *Attorney, Agent, or Firm* — Brundidge & Stanger, P.C.

(57) ABSTRACT

A semantic medical technology is disclosed. In various embodiments, the technology organizes an initial data collection to collect data from the one or more sensors; processes the data to obtain an initial diagnosis wherein the initial diagnosis can be a syntax diagnosis or a semantic diagnosis; identifies an organization for an additional data collection to collect additional data; analyzes the additional data to obtain a refined diagnosis; and repeats the identifying and analyzing until a stopping criterion is satisfied.

20 Claims, 7 Drawing Sheets

(56) References Cited

U.S. PATENT DOCUMENTS

| | | | |
|---|---|---|---|
| 2005/0244069 A1 | 11/2005 | Wang | |
| 2005/0256974 A1 | 11/2005 | Teodosiu et al. | |
| 2005/0265616 A1 | 12/2005 | Rose | |
| 2006/0063156 A1 | 3/2006 | Willman et al. | |
| 2006/0104526 A1 | 5/2006 | Gringeler et al. | |
| 2006/0129324 A1 | 6/2006 | Rabinoff et al. | |
| 2006/0224059 A1* | 10/2006 | Swedlow et al. | 600/323 |
| 2007/0004466 A1* | 1/2007 | Haartsen | 455/572 |
| 2007/0079223 A1 | 4/2007 | Mondin et al. | |
| 2007/0096954 A1 | 5/2007 | Boldt et al. | |
| 2007/0233623 A1 | 10/2007 | Vatchkov et al. | |
| 2008/0004904 A1 | 1/2008 | Tran | |
| 2008/0050025 A1 | 2/2008 | Bashyam et al. | |
| 2008/0187047 A1 | 8/2008 | Stephan et al. | |
| 2009/0037220 A1* | 2/2009 | Chambers et al. | 705/3 |
| 2009/0069642 A1 | 3/2009 | Gao et al. | |
| 2009/0124917 A1* | 5/2009 | Hatlestad et al. | 600/529 |
| 2009/0177495 A1* | 7/2009 | Abousy et al. | 705/3 |
| 2009/0228299 A1 | 9/2009 | Kangarloo et al. | |
| 2009/0312817 A1 | 12/2009 | Hogle et al. | |
| 2010/0008424 A1 | 1/2010 | Pace | |
| 2010/0046848 A1 | 2/2010 | Witzgall et al. | |
| 2010/0063365 A1* | 3/2010 | Pisani et al. | 600/301 |
| 2010/0076714 A1 | 3/2010 | Discenzo | |
| 2011/0251986 A1 | 10/2011 | Potkonjak | |
| 2012/0265737 A1 | 10/2012 | Potkonjak | |
| 2012/0265738 A1 | 10/2012 | Beckmann et al. | |

OTHER PUBLICATIONS

Anderson et al, "Shakra: tracking and sharing daily activity levels with unaugmented mobile phones," Mobile Networks and Applications, v.12 n.2-3, p. 185-199, Mar. 2007.

Consolvo, Sunny et al., "Design requirements for technologies that encourage physical activity," Proceedings of the SIGCHI conference on Human Factors in computing systems, Apr. 2006.

Danninger et al., "The connector: facilitating context-aware communication," Proceedings of the 7th Int'l conference on Multimodal Interfaces, Oct. 2005.

Driver, Cormac and Siobhan Clarke, "An application framework for mobile, context-aware trails," Pervasive and Mobile Computing, v.4 n.5, p. 719-736, Oct. 2008.

Hand, E., "Head in the clouds," Nature, vol. 449, Oct. 24, 2007, p. 963.

Harrison, Chris et al., "Lightweight material detection for placement-aware mobile computing," Proceedings of ACM symposium on User interface software and technology, Oct. 2008.

Hayes, Brian, "Cloud computing," Communications of the ACM, v.51 n.7, Jul. 2008.

International Search Report for PCT/US2010/030952 filed Apr. 13, 2010; Applicant: Empire Technology Development LLC, mailed Dec. 12, 2011.

Iso et al., "Gait analyzer based on a cell phone with a single three-axis accelerometer," Proceedings of the 8th conference on Human-computer interaction with mobile devices and services, Sep. 2006.

Istepanian, R.S.H. and S. Laxminaryan, "UNWIRED, the next generation of wireless and internetable telemedicine systems—editorial paper," IEEE Trans. Inform. Technol. Biomed., vol. 4, pp. 189-194, Sep. 2000.

Jovanov, E. et al., "Stress monitoring using a distributed wireless intelligent sensor system," IEEE Eng. Med. Biol. Mag., vol. 22, No. 3, pp. 49-55, May/Jun. 2003.

Khalil et al., "Context-aware telephony: privacy preferences and sharing patterns," Proceedings of the conference on Computer supported cooperative work, Nov. 2006.

Korhonen, I. et al., "Health monitoring in the home of the future," IEEE Eng. Med. Biol. Mag., vol. 22, No. 3, pp. 66-73, May/Jun. 2003.

Kurdi, Heba et al., "A Classification of Emerging and Traditional Grid Systems," IEEE Distributed Systems Online, v.9 n.3, p. 1, Mar. 2008.

Lederer, Scott et al., "Personal privacy through understanding and action: five pitfalls for designers," Personal and Ubiquitous Computing, v.8 n.6, p. 440-454, Nov. 2004.

Park, S. and S. Jayaraman, "Enhancing the quality of life through wearable technology," IEEE Eng. Med. Biol. Mag., vol. 22, No. 3, pp. 41-48, May/Jun. 2003.

Pattichis, C. S. et al., "Wireless telemedicine systems: An overview," IEEE Antennas Propagat. Mag., vol. 44, No. 2, pp. 143-153, Apr. 2002.

Robison, S., "A Bright Future in the Cloud," Financial Times, Mar. 4, 2008.

Rochwerger, B. et al., "The reservoir model and architecture for open federated cloud computing," IBM Systems Journal, vol. 53, No. 4, 2009.

Siewiorek et al., "A Context-Aware Mobile Phone," Proceedings of the 7th IEEE Int'l Symposium on Wearable Computers, pp. 248-249, 2003.

Stanford, V., "Using pervasive computing to deliver elder care," IEEE Pervasive Computing, vol. 1, pp. 10-13, Jan./Mar. 2002.

Valdastri, P. et al., "An implantable telemetry platform system for in vivo monitoring of physiological parameters," IEEE Trans. Inform. Technol. Biomed., vol. 8, No. 3, pp. 271-278, Sep. 2004.

Bai et al. "Segmentation-based multilayer diagnosis lossless medical image compression" Australian Computer Society, Inc. Darlinghurst, Australia, Australia 2004.

Doukas et al. "Context-Aware Medical Content Adaptation through Semantic Representation and Rules Evaluation" 3rd International Workshop on Semantic Media Adaptation and Personalization, 22 pages, 2008.

Gallager, R., "Variations on a Theme by Huffman," IEEE Transactions on Information Theory, vol. IT-24, No. 6, Nov. 1978, 7 pages.

International Search Report and Written Opinion; International Application No. PCT/US10/30950; Filed Apr. 13, 2010; Applicant: Empire Technologies Development LLC; Mailed Sep. 23, 2010; 10 pages.

International Search Report and Written Opinion; International Application No. PCT/US10/30953; Filed Apr. 13, 2010; Applicant: Empire Technologies Development LLC; Mailed Aug. 4, 2010; 11 pages.

International Search Report for PCT/US2010/030954 filed Apr. 13, 2010; Applicant: Empire Technology Development, LLC; mailed Aug. 25, 2010.

Kanefsky, M. & C-B Fong, "Predictive source coding techniques using maximum likelihood prediction for compression of digitized images," IEEE Transactions on Information Theory, vol. 30, Issue 5, pp. 722-727, Sep. 1984.

Le Gall, Didier, "MPEG: a video compression standard for multimedia applications," Communications of the ACM, v.34 n.4, p. 46-58, Apr. 1991.

Ogiela et al. "Nonlinear processing and semantic content analysis in medical imaging—a cognitive approach" Inst. of Autom., AGH Univ. of Sci. & Technol., Krakow, Poland, Dec. 2005.

Rissanen, J., "Generalised Kraft inequality and arithmetic coding," IBM J. Res. Dev. 20, 198-203, 1976.

Sahay et al. "Semantic Annotation and Inference for Medical Knowledge Discovery" NSF Symposium on Next Generation of Data Mining(NGDM), Baltimore, NSF Symposium Proceedings, 2007.

Shapiro, J., "Embedded Image Coding Using Zerotrees of Wavelet Coefficients," IEEE Transactions on Signal Processing, vol. 41, No. 12, Dec. 1993, 18 pages.

Wallace, Gregory K., "The JPEG still picture compression standard," Communications of the ACM, v.34 n.4, p. 30-44, Apr. 1991.

Witten et al. "Arithmetic coding for data compression," Communications of the ACM, v.30 n.6, p. 520-540, Jun. 1987.

Zhang et al., "An on-line universal glossy data compression algorithm via continuous codebook refinement. I. Basic results," Information Theory, IEEE Transactions on, vol. 42, pp. 803-821, 1996.

Ziv et al., "A Universal Algorithm for Sequential Data Compression," IEEE Transactions on Information Theory, vol. IT-23, No. 3, May 1977, 7 pages.

\* cited by examiner

SEMANTIC MEDICAL DEVICES

CROSS-REFERENCE TO RELATED APPLICATIONS

This application is a U.S. National Stage application filing under 35 U.S.C. §371 of International Application No. PCT/US2010/030952, filed on Apr. 13, 2010, entitled "SEMANTIC MEDICAL DEVICES," which is incorporated herein by reference in its entirety.

BACKGROUND

Computing devices have become commonplace and indeed nearly ubiquitous. A typical home now has multiple computing devices, e.g., laptop computers, desktop computers, media servers, media players, mobile telephones, etc. Many of these computing devices are interconnected via a local area network, whether wired or wireless, and even to remote computing devices via the Internet.

As modern medicine advances, it has come to rely on computing devices for various functions, e.g., record keeping and remote radiological assessments. A medical facility may attach several sensors to an ailing or recovering patient, e.g., heart rate monitor, blood pressure monitor, electrocardiograph (EKG) monitor, blood content monitor, urine analysis monitor, brain activity monitor, various other electrodes, etc. When in the medical facility, medical practitioners (e.g., physicians, nurses, etc.) may monitor a patient using computing devices that receive signals from these and other sensors.

Software executing on computing devices can employ data collected from the sensors to conduct various medical assessments, such as by producing preliminary diagnoses, alerting medical practitioners, or taking other actions. However, when the patient leaves the medical facility, it is difficult to continue the medical assessments.

SUMMARY

A semantic medical technology is disclosed. The technology can organize an initial data collection to collect data from the one or more sensors; process the data to obtain an initial diagnosis wherein the initial diagnosis can be a syntax diagnosis or a semantic diagnosis; identify an organization for an additional data collection to collect additional data; analyze the additional data to obtain a refined diagnosis; and repeat the identifying and analyzing until a stopping criterion is satisfied.

DETAILED DESCRIPTION

Figure 1:
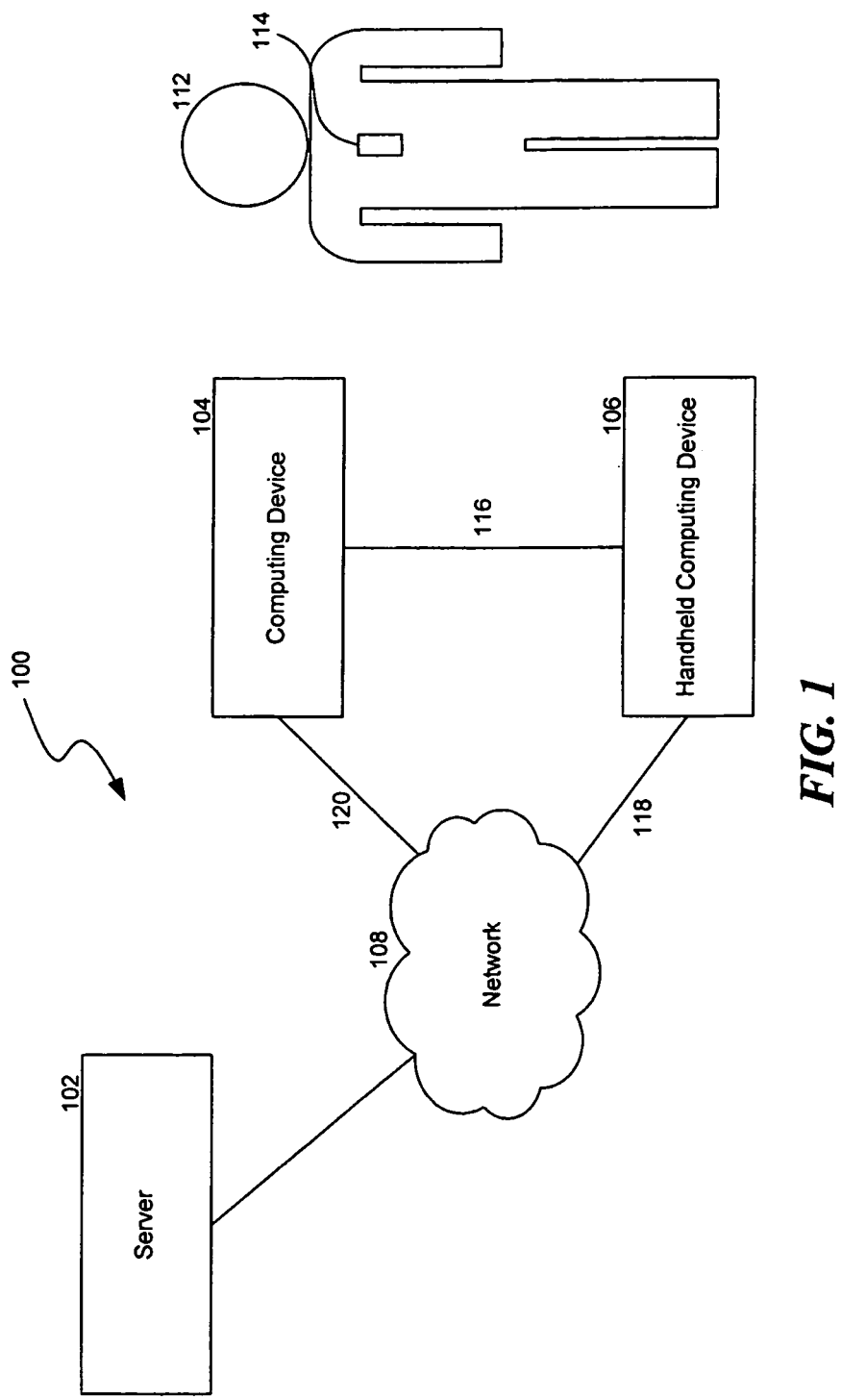
FIG. 1 is a block diagram illustrating an environment in which a semantic medical technology can operate in some embodiments.

Semantic medical technology is disclosed. In various embodiments, the semantic medical technology collects data from sensors, identifies a computing device for processing the collected data, and transmits the collected data for analysis. The semantic medical technology can include a handheld computing device, e.g., a mobile telephone, personal digital assistant, digital watch, wearable computer, etc. The handheld computing device may monitor and/or receive patient-related data. As examples, the handheld computing device may receive data from sensors attached to a patient, e.g., a heart rate monitor, blood pressure monitor, blood monitor, etc. The handheld computing device may also have built-in sensors, e.g., temperature monitor, breath monitor, brainwave monitor, etc. As the handheld computing device collects the data, it may perform an initial assessment of the patient. As an example, if the patient's temperature is rising rapidly, the handheld computing device may automatically determine whether to transmit the collected data to another computing device, alert the patient, alert a medical practitioner, etc. The handheld computing device may make this determination based on various factors including, e.g., semantic processing, context, or resolution.

In some embodiments, the semantic medical technology can perform semantic processing of the collected data so as to determine what other data may be relevant. As an example, when a patient's temperature is increasing, the semantic medical technology can collect other data from sensors associated with the patient to determine whether the patient is likely getting dehydrated or about to have a heart attack. If the patient is about to have a heart attack (or requires other urgent medical attention), the semantic medical technology can alert a medical service provider and/or the patient (e.g., by making a phone call, raising an alarm, etc.) In various embodiments, the semantic medical technology collects data in a context-aware manner. As an example, if the patient's temperature is rising and the patient is involved in some physical exertion, the semantic medical technology may determine that a blood monitor reading is not required. In various embodiments, the semantic medical technology is capable of determining a "resolution" for data, e.g., periodicity of data collection or sensitivity of the sensors. By identifying appropriate sensors for collecting data based on context, varying data collection resolution, and semantically processing the collected data, the semantic medical technology optimizes the use of data collection, transmission, and diagnosis resources.

In some embodiments, the semantic medical technology may determine to which computing device to route collected data based on computing and latency requirements. As an example, if a large volume of data needs to be analyzed with reference to a large volume of historical data, a server may be appropriate. Alternatively, if very low communications latency is desirable (e.g., in the event of an impending catastrophic event), a handheld computing device near the patient may be desirable.

In various embodiments, the semantic medical technology may apply maximum likelihood estimation (MLE) techniques. As an example, the semantic medical technology may identify patterns in signals and determine where to send the data for analysis based on a prediction of diagnoses derived from an MLE analysis.

In various embodiments, the semantic medical technology can make decisions to facilitate diagnosis and/or treatment.

As examples, the semantic medical technology can determine to which computer the data should be transmitted for analysis based on various factors, e.g., availability of a data transmission medium, data transmission latency, expected battery life, accuracy of computation, speed of computation, location of other needed data, privacy, etc.

In various embodiments, a system of sensors, including scanners, computing devices, communication devices, and actuating devices automatically determines how best to conduct organization, data collection, data processing, data communication and storage to facilitate diagnosis and/or treatment of a subject (e.g., patient) using the medical record and preliminary medical findings and the overall status of various equipment.

Figure 7:
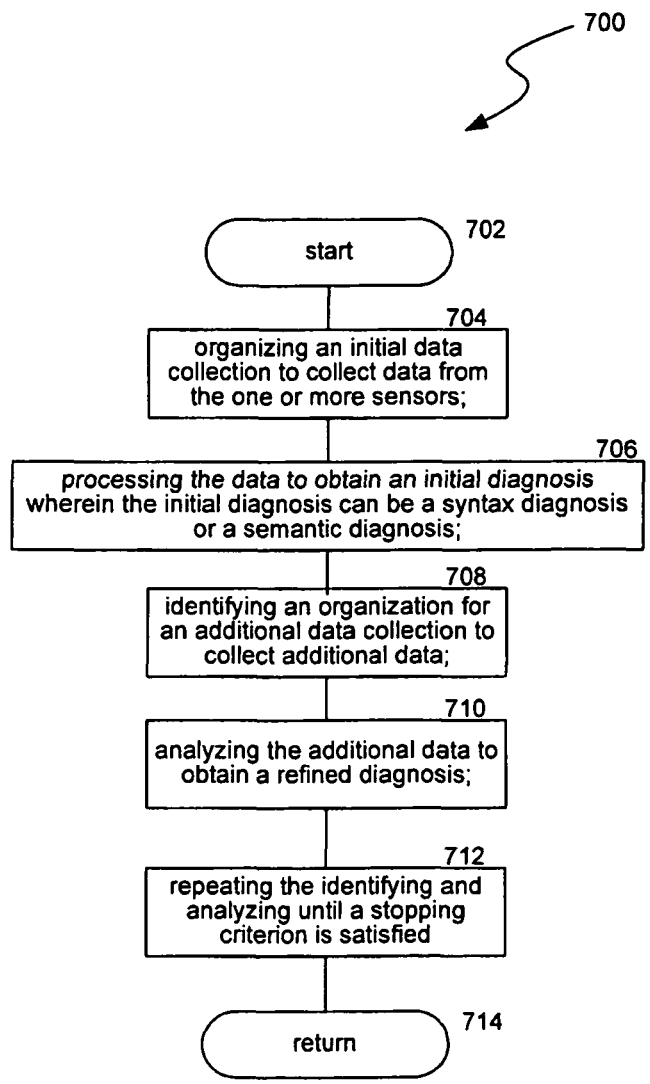
FIG. 7 is a flow diagram illustrating a routine invoked by the semantic medical technology in some embodiments.

In various embodiments, the technology implements a method 700 (see, e.g., FIG. 7) performed by a computing system having a processor and memory for organizing data collection and processing from one or more sensors. The method begins at block 702 and comprises: organizing an initial data collection to collect data from the one or more sensors (704); processing the data to obtain an initial diagnosis wherein the initial diagnosis can be a syntax diagnosis or a semantic diagnosis (706); identifying an organization for an additional data collection to collect additional data (708); analyzing the additional data to obtain a refined diagnosis (710); and repeating the identifying and analyzing until a stopping criterion is satisfied (712). At block 714, the method returns. The determining can be based using at least one or more of semantic processing of collected data, context processing of collected data, semantic and context processing of collected data, information about a subject proximate to the one or more sensors, urgency of a required response, information about a current or future availability of expert personnel, a cost, or a status of equipment used for the data collection or processing. The determining can include at least partly considering geolocation, time, activities of a subject proximate to the one or more sensors, other context data, or a model. Organizing the data collection can include using expected signals from the one or more sensors and operational conditions of sensing equipment. Processing the data can include processing one or more of radiation intensity, resolution, exposition, sampling rate, or other operational characteristics of actuators or sensors, and semantically analyzing an importance and relevance of data from the one or more sensors. Organizing and the identifying can include semantically evaluating one or more detected events, statuses, trends or conditions of either or both of (a) an observed subject proximate to the one or more sensors or (b) equipment. The stopping criterion can be a likelihood that collecting additional data would change conclusions about events, statuses, trends or conditions of a subject proximate to the one or more sensors.

In various embodiments, the technology can be implemented on one or more apparatuses, comprising: a processor and memory; means for organizing an initial data collection to collect initial data; means for identifying a computing device at which the initial data is to be processed and a function for processing the initial data; means for optionally communicating the initial data to another computing device; means for processing the initial data to obtain an initial syntax diagnosis, semantic diagnosis, or both; means for identifying an organization for an additional data collection to collect additional data; and means for performing local data analysis and optionally coordinating with remote data analysis to obtain a refined diagnosis, wherein the refined diagnosis is a syntax diagnosis, semantic diagnosis, or both. At least some of the processing may be performed by a remote computing device. The apparatuses can further comprise means for receiving a diagnosis from a human operator or an expert system. The processor and memory can be embodied in a sensor node, a handheld computing device (e.g., personal digital assistant, mobile phone, tablet, etc.), or a computer in a data center.

In various embodiments, the technology implements a method of determining how to process data collected from sensors, comprising: receiving at a first computing device data from a sensor; determining automatically from the data whether analysis of the data is urgent; if the analysis is urgent, determining whether latency can be tolerated; if latency can be tolerated, forwarding the data to a second computing device; if latency cannot be tolerated, analyzing the data; and if the analysis is not urgent, forwarding the data to a third computing device. The method can further comprise instructions for: determining whether or not to forward the data partly or fully based on power consumption required for transmission and estimated or measured remaining power at each device the data will transit; and if data is to be forwarded, calculating an optimal organization for the data transmission including a subset of a set of parameters. The parameters can be, e.g., the transmission power, type of modulation, employed error correction code, the length of the packets, time of transmission, etc. The method can further comprise instructions for determining whether or not to forward the data based on whether a patient needs to be notified immediately. The method can further comprise instructions for determining whether or not to forward the data based on a patient's heart conditions including heart rate, blood pressure, or both. The method can further comprise instructions for determining how to organize data collection and its analysis in such a way that estimated harmful effects to the subject is minimized.

The technology can include a system for determining how to collect and process data collected from sensors, comprising: one or more sensors configured to collect data, at least some of the one or more sensors having a transceiver; an analyzer placed on one or more sensors and configured to determine whether to analyze the data or to forward the data for analysis, wherein the analyzer is configured to determine whether or not to forward the data based on a computation of urgency, the urgency computed based on the data; a computing device having a processor, memory, transceiver, optionally one or more sensors, and an analyzer and configured to determine whether to analyze data the computing device receives or to forward the received data for analysis, wherein the analyzer determines whether or not to forward the data based on a computation of urgency, expect benefits, cost, or other function.

The technology can include a system for determining how to collect and process data collected from sensors, comprising: one or more sensors configured to collect data, at least some of the one or more sensors having a transceiver; one or more computing devices having one or more transceivers; one or more storage devices each with a communication interface; one or more actuators for data collection; one or more communication devices; system software required to operate each device; communication software required to coordinate tasks at different devices; and application software required for data collection and analysis. The system may include one or more components that are shared for monitoring and treatment of multiple subjects.

In various embodiments, the semantic medical technology provides techniques, models, algorithms, and tools for the design and deployment of various systems for analysis of a mix of subjects that are treated by the disclosed technology;

design and/or selection of specific deployment of stationary devices; deployment of mobile devices; optimization of composite objective function that includes a subset or a superset of entities such as the accuracy of diagnosis; estimate potential harmful consequences, cost, and operational lifetime.

The technology will now be described with reference to the Figures ("drawings"). In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 is a block diagram illustrating an environment 100 in which a semantic medical technology can operate in some embodiments. The environment 100 can include one or more server computing devices 102, client computing devices 104, and handheld computing devices 106. Each of the computing devices 102, 104, and 106 may be interconnected, such as via a network 108. The interconnections can be wired or wireless. As an example, computing device 104 may be connected via a wired connection 120 with network 108. Handheld computing device 106 may be interconnected with computing device 104 and network 108 via wireless connections 116 and 118. Handheld computing device 106 may receive data from a sensor 114 attached to a patient 112. As an example, handheld computing device 106 may receive data from a heart rate monitor attached to patient 112.

In various embodiments, server 102, computing device 104, and handheld computing device 106 may have different computational capabilities, access to historical patient data, access to other data (e.g., diagnostic data), and communications or processing latencies.

Figure 2:
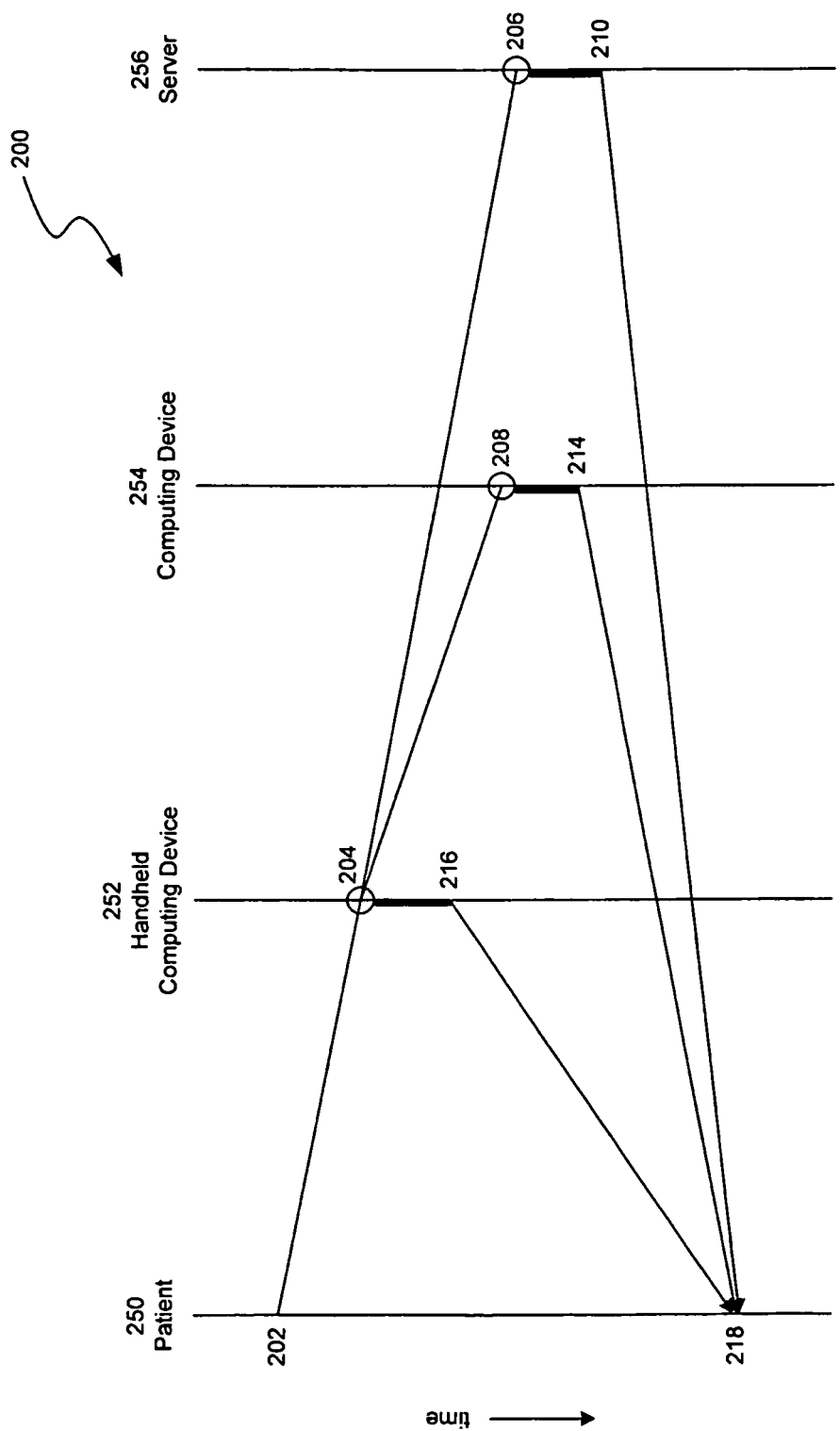
FIG. 2 is a data flow diagram illustrating operation of the semantic medical technology in some embodiments.

FIG. 2 is a data flow diagram illustrating operation of the semantic medical technology in some embodiments. A data flow 200 can begin at a sensor attached to a patient 250 that produces data 202. The data may be received by a handheld computing device 252. Handheld computing device 252 can make a determination 204 of whether to analyze the data or forward the data to another computing device for analysis. As an example, handheld computing device 252 can determine whether the analysis of the data is urgent. If analysis is not urgent, handheld computing device 252 may forward the data to a computing device 254 (e.g., a home gateway) for a determination 208. Alternatively, if analysis is urgent but some latency is tolerable, handheld computing device 252 may forward the data to a remote server 256, e.g., via a network such as the Internet, for a determination 206. If analysis is urgent and immediate notification to patient 250 is required (e.g., latency is intolerable), handheld computing device 252 may analyze 216 the data and provide an analysis to patient 250 via an output 218. Computing device 254 can analyze the data 214 and provide an analysis to patient 250 via output 218. Server 256 can analyze the data 210 and provide an analysis to patient 250 via output 218. The bolded line segments between receipt of data and transmission of data is indicative of processing. As an example, the bolded line segment between elements 204 and 216 of the figure is indicative of analysis performed by handheld computing device 252.

Handheld computing device 252 may make its determination 204 based on various factors, such as urgency, latency requirements, power consumption/remaining battery life, etc. As an example, if the patient's heart rate exceeds a specified threshold, handheld computing device 252 may increase a resolution of monitoring the heart rate without regard to power consumption. Alternatively, if the patient's temperature is steady, handheld computing device may determine that latency is tolerable and transmit the data to computing device 254 or server 256.

Handheld computing device 252 may also make its determination 204 based on semantic processing of the data. As an example, if the data indicates that patient 250 may be undergoing a heart attack, handheld computing device 252 may analyze 216 the data and notify patient 250 via output 218 to immediately seek medical attention. Handheld computing device 252 may also notify emergency medical technicians, e.g., by dialing 911.

Handheld computing device 252 may also make its determination 204 based on context. As examples of context, handheld computing device 252 may determine that its present geolocation is in a gym (e.g., based on a GPS signal), patient 250 is exerting force or participating in physically strenuous activity (e.g., based on rapid fluctuations experienced by an accelerometer), etc. In such a case, handheld computing device 252 may determine that a rapidly increasing heart rate that does not exceed a specified threshold value does not need to be urgently reported or analyzed.

To deal with latency and power consumption as the computational power and data availability increases across the various computing platforms the semantic medical technology employs, the semantic medical technology employs multi-resolution decision processing. As an example, at handheld computing device 252, the semantic medical technology analyzes a portion of the received data for semantic meaning so as to determine urgency and the tolerance for latency. As the data is moved to a home gateway (e.g., another computing device), the semantic medical technology increases the resolution of the decision processing. Similarly, as data is moved to a server, the resolution of the decision processing may be at a maximum.

The semantic medical technology can assume that the data from the body has a normal distribution and that data collected from various sensors is independent of each other. The semantic medical technology can employ a maximum likelihood approach to determine the likelihood of a particular health condition. As an example, electrocardiogram (ECG) signals obtained from a patient using wearable electrodes may provide heart rate information as "R-wave events," or heart beats, over time. A statistical measure of heart rate is an "R-R peak distance" or an "R-R interval," and can be used to determine whether the patient has a healthy heart beat. The semantic medical technology can employ a maximum likelihood estimator to estimate the likelihood of a dangerous distance between the R-R peaks. If the distance is estimated to fall within a dangerous range, then the semantic medical technology can send an emergency message to a medical practitioner (e.g., physician), alert the patient to take medication, etc. Otherwise, the semantic medical technology can transfer the data to another computing device for additional analysis, combination with other signal data, application of context information for proper processing, etc.

Those skilled in the art will appreciate that the steps shown in FIG. 2 and in each of the flow diagrams discussed herein may be altered in a variety of ways. For example, the order of the logic may be rearranged; substeps may be performed in parallel; shown logic may be omitted, or other logic may be included; etc. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 3:
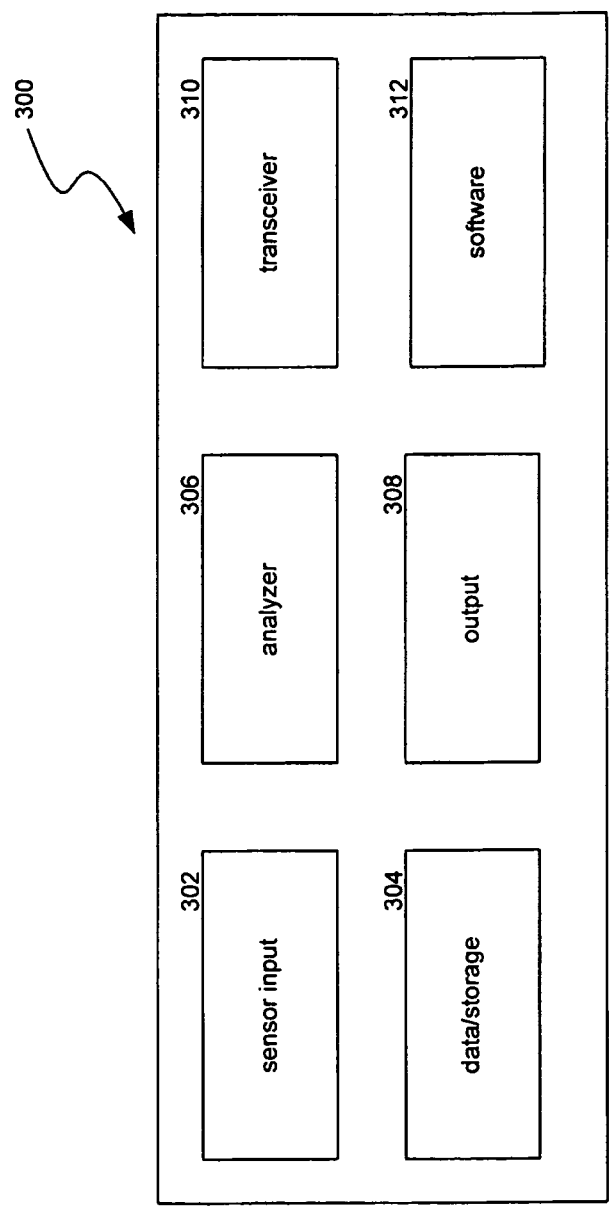
FIG. 3 is a block diagram illustrating components of the semantic medical technology in various embodiments.

FIG. 3 is a block diagram illustrating components 300 of the semantic medical technology in various embodiments. Components 300 can include a sensor input 302, data/storage 304, an analyzer 306, an output 308, and a transceiver 310. Sensor input 302 can receive data from one or more sensors, e.g., sensors attached to a patient. The sensors may transform one or more physical attributes of a patient into data. Examples of sensors include blood monitors, blood pressure monitors, temperature monitors, urine/stool monitors, etc. The received data can be stored on data/storage 304. Analyzer 306 can analyze the received data, e.g., stored on data/storage 304, and provide output via an output component 308. Transceiver 310 can send or receive data communications, e.g., via a wireless or wired network (not illustrated). The technology may also implement and/or employ other software 312.

Figure 4:
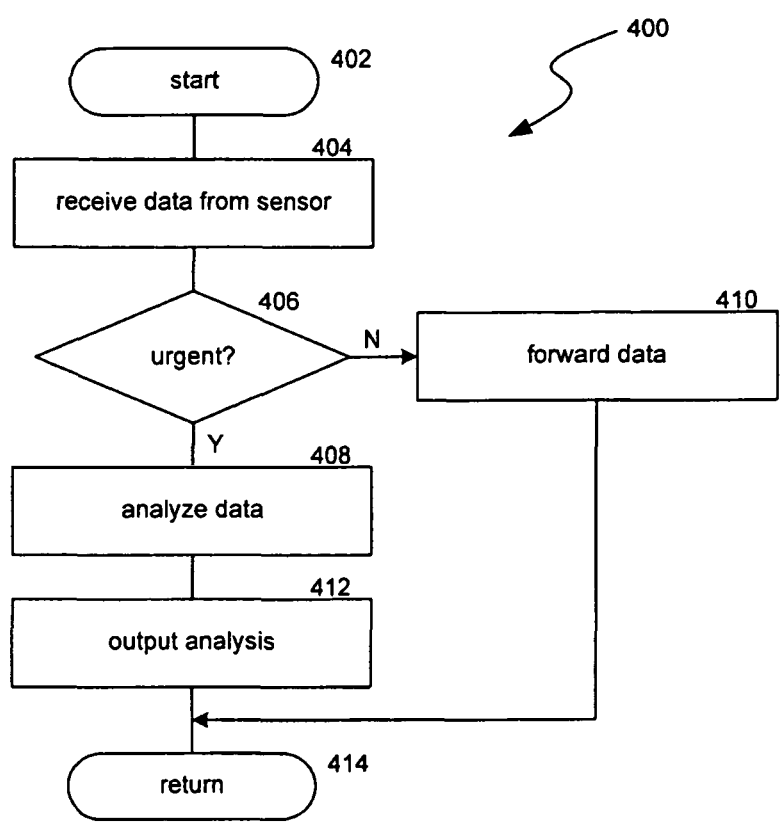
FIG. 4 is a flow diagram illustrating a routine invoked by the semantic medical technology in some embodiments.

FIG. 4 is a flow diagram illustrating a routine 400 invoked by the semantic medical technology in some embodiments. The routine begins at block 402. At block 404, the routine receives data from a sensor. At decision block 406, the routine determines whether the received data should be urgently analyzed or forwarded. If the data should be urgently analyzed or forwarded, the routine continues at block 408. Otherwise, the routine continues at block 410. At block 408, the routine analyzes the data. In some embodiments, the routine may alternatively forward the data to a server for analysis. At block 412, the routine outputs the analysis, e.g., by notifying a patient or a medical practitioner, etc. At block 410, the routine forwards the data, e.g., to another computing device. As an example, the routine may forward the data to a computing device via a server. At block 414, the routine returns.

Figure 5:
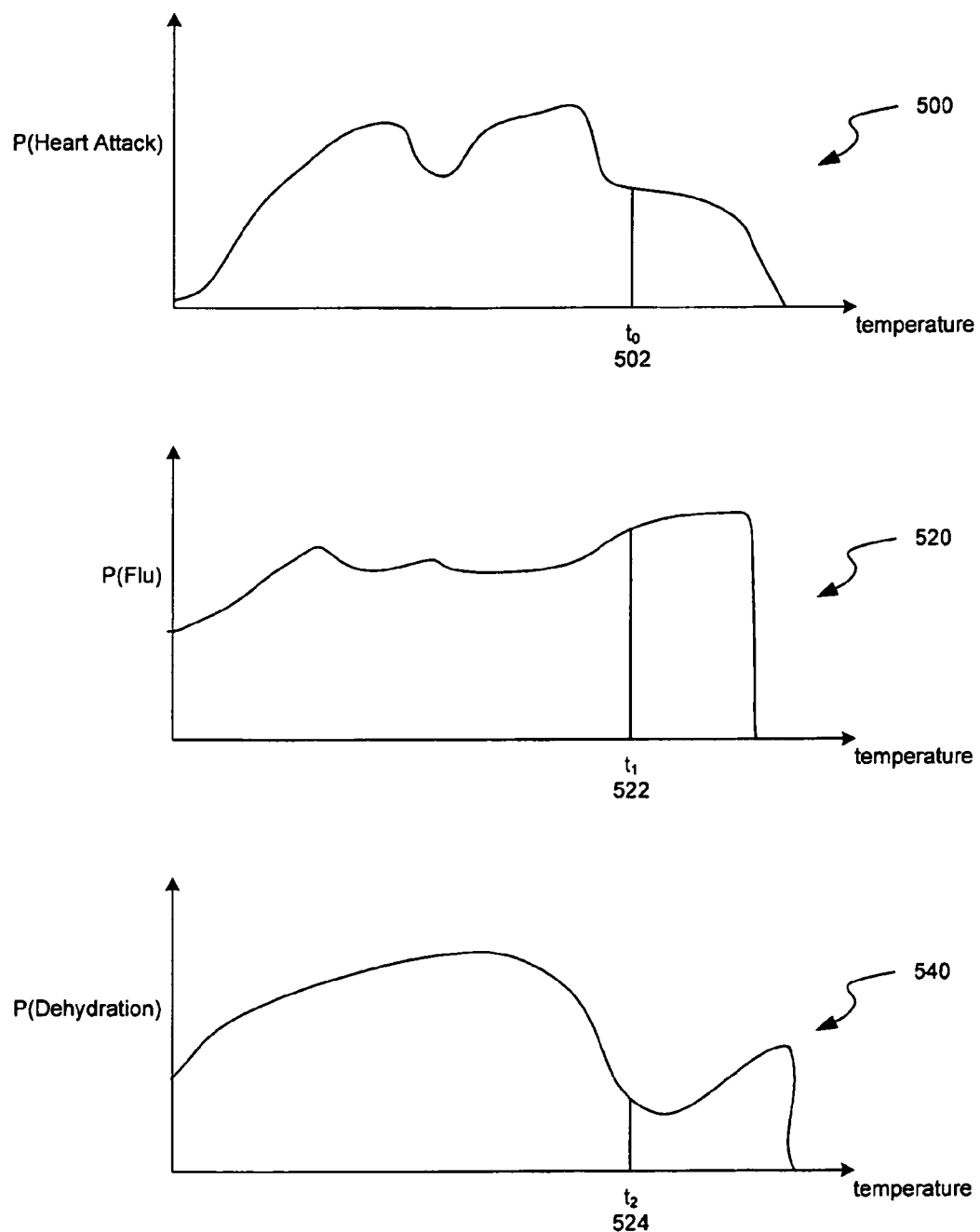
FIG. 5 is a probability distribution diagram illustrating various probabilities of preliminary diagnoses associated with data received from a sensor in various embodiments.

FIG. 5 is a probability distribution diagram illustrating various probabilities of preliminary diagnoses associated with data received from a sensor in various embodiments. As depicted, a probability distribution diagram 500 indicates the probability of a heart attack for any given temperature; a probability distribution diagram 520 indicates the probability of a flu for any given temperature; and a probability distribution diagram 540 indicates the probability of a dehydration for any given temperature. As an example, at a temperature $t_0$ 502, $t_1$ 522, or $t_2$ 524, the probability of the flu is highest. In some embodiments, the semantic medical technology may combine the probabilities by computing the product of all three probabilities.

Figure 6:
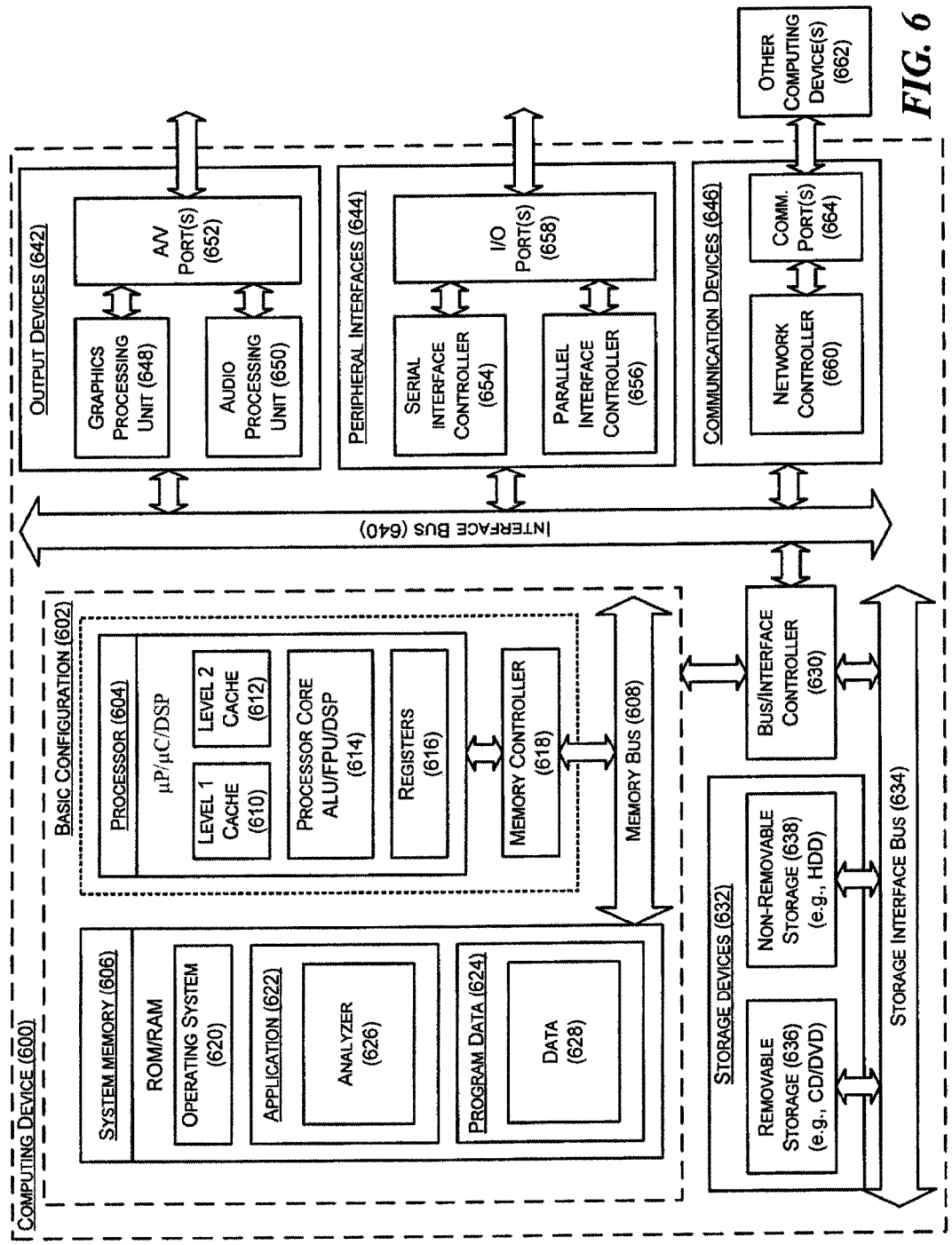
FIG. 6 is a block diagram illustrating an example of a computing device that can be arranged as a suitable computing system for use with the semantic medical technology in accordance with the present disclosure.

FIG. 6 is a block diagram illustrating an example of a computing device 600 that can be arranged as a suitable computing system for use with the feedback technology in accordance with the present disclosure. In a very basic configuration 602, computing device 600 typically includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include one or more components (e.g., an analyzer 626) that are arranged to analyze data, determine urgency, etc. The software components may employ hardware devices, such as sensors. Program data 624 may include data 628 that may be useful for generating diagnoses. In some embodiments, application 622 may be arranged to operate with program data 624 on operating system 620. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or other specific examples or embodiments disclosed herein. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method performed by a computing system having a processor and memory to obtain analysis of data collected from one or more sensors, comprising:

organizing, by a first computing device, data collected from the one or more sensors;

determining, by the first computing device, from among a plurality of candidate computing devices for analysis of the data that include the first computing device, a computing device for analysis of the data, the determining based at least in part on power consumption required for sending the data to one of the plurality of candidate computing devices other than the first computing device and remaining power at the one of the plurality of candidate computing devices;

in response to the first computing device determining that the computing device for analysis of the data is the first computing device, analyzing the data by the first computing device;

in response to the first computing device determining that the computing device for analysis of the data is other than the first computing device, sending the data by the first computing device for the determined computing device for analysis of the data.

2. The method of claim 1,
wherein the determining includes one or more of semantic processing of the data or context processing of the data; and
wherein the data includes at least one of information about a subject proximate to the one or more sensors, information about a current or future availability of expert personnel, a cost, or a status of equipment used for the data collection or processing.

3. The method of claim 2, wherein the data further includes at least one of geolocation, time, activities of a subject proximate to the one or more sensors, or a model.

4. The method of claim 1, wherein organizing the data includes using expected signals from the one or more sensors and operational conditions of sensing equipment.

5. The method of claim 2,
wherein the data further includes one or more of radiation intensity, resolution, exposition, sampling rate, or other operational characteristics of actuators or sensors, and
wherein the semantic processing includes semantically analyzing an importance and relevance of data from the one or more sensors.

6. The method of claim 2, wherein the semantic processing includes semantically evaluating one or more detected events, statuses, trends or conditions of either or both of (a) an observed subject proximate to the one or more sensors or (b) equipment.

7. An apparatus, comprising:
a processor and memory;
means for organizing data;
means for determining, from among a plurality of candidate computing devices for analysis of the data that include the processor, a computing device for analysis of the data, the determining based at least in part on power consumption required for sending the data to one of the plurality of candidate computing devices other than the processor and remaining power at the one of the plurality of candidate computing devices;
means for performing local data analysis, including analysis of the data, in response to determining that the computing device for analysis of the data is the processor; and
means for sending data, including sending the data for the determined computing device for analysis of the data in response to determining that the determined computing device for analysis of the data is other than the processor.

8. The apparatus of claim 7, further comprising means for receiving a diagnosis from a human operator or an expert system.

9. The apparatus of claim 7, wherein the processor and memory are embodied in one of a sensor node, a handheld computing device, or a computer in a data center.

10. An apparatus, comprising:
a processor and memory; and
a communication interface;
wherein the processor is configured to:
organize data;
determine, from among a plurality of candidate computing devices for analysis of the data that include the processor, a computing device for analysis of the data, based at least in part on power consumption required for sending the data to one of the plurality of candidate computing devices other than the processor and remaining power at the one of the plurality of candidate computing devices;
control analysis of the data in response to determining that the computing device for analysis of the data is the processor; and
send, via the communication interface, the data for the determined computing device for analysis of the data in response to determining that the determined computing device for analysis of the data is other than the processor.

11. The apparatus of claim 10, wherein the processor is further configured to receive, via the communication interface, a diagnosis from a human operator or an expert system.

12. The apparatus of claim 10, wherein the processor and memory are embodied in one of a sensor node, a handheld computing device, or a computer in a data center.

13. The apparatus of claim 10, wherein the processor is further configured to:
perform one or more of semantic processing of the data or context processing of the data;
wherein the data includes at least one of information about a subject proximate to one or more sensors from which the data is collected, information about a current or future availability of expert personnel, a cost, or a status of equipment used for the data collection or processing; and
wherein determining of the computing device for analysis of the data is further based on the one or more of semantic processing or context processing of the data.

14. The apparatus of claim 13, wherein the data further includes at least one of geolocation, time, activities of a subject proximate to one or more sensors from which the data is collected, or a model.

15. The apparatus of claim 10, wherein organizing the data includes using expected signals from one or more sensors from which the data is collected and operational conditions of sensing equipment.

16. The apparatus of claim 13, wherein the data further includes one or more of radiation intensity, resolution, exposition, sampling rate, or other operational characteristics of actuators or sensors, and
wherein the one or more of semantic processing or context processing of the data includes semantically analyzing an importance and relevance of data from one or more sensors from which the data is collected.

17. The apparatus of claim 13, wherein the one or more of semantic processing or context processing includes semantically evaluating one or more detected events, statuses, trends or conditions of either or both of (a) an observed subject proximate to one or more sensors from which the data is collected or (b) equipment.

18. The method of claim 1, wherein the determining of a computing device for analysis of the data includes:
analyzing, by the first computing device, a portion of the data that is less than all of the data; and
determining whether the computing device for analysis of the data is the first computing device or other than the first computing device based on the analyzing of the portion of the data.

19. The apparatus of claim 7,
wherein the means for performing local data analysis is further for performing analysis of a portion of the data that is less than all of the data; and
wherein the means for determining is further for determining whether the computing device for analysis of the data is the processor or other than the processor based on the analyzing of the portion of the data.

20. The apparatus of claim 10, wherein the processor is further configured to:

control analysis of a portion of the data that is less than all of the data; and determine whether the computing device for analysis of the data is the processor or other than the processor based on the analyzing of the portion of the data.

\* \* \* \* \*